United States Patent
Oddos et al.

(10) Patent No.: US 7,928,142 B2
(45) Date of Patent: Apr. 19, 2011

(54) COMPOSITIONS CONTAINING RETINOID AND BETA-AMINOISOBUTYIC ACID DERIVATIVES

(75) Inventors: Thierry Oddos, Menden (FR); Otto Von Stetten, Aachen (DE)

(73) Assignee: Johnson & Johnson Consumer France SAS (FR)

( * ) Notice: Subject to any disclaimer, the term of this patent is extended or adjusted under 35 U.S.C. 154(b) by 379 days.

(21) Appl. No.: 12/041,999

(22) Filed: Mar. 4, 2008

(65) Prior Publication Data

US 2009/0017104 A1      Jan. 15, 2009

(30) Foreign Application Priority Data

Mar. 20, 2007    (EP) .................................... 07290337

(51) Int. Cl.
| | |
|---|---|
| *A01N 37/30* | (2006.01) |
| *A01N 37/12* | (2006.01) |
| *A01N 37/44* | (2006.01) |
| *A01N 31/04* | (2006.01) |
| *A61K 31/205* | (2006.01) |
| *A61K 31/195* | (2006.01) |
| *A61K 31/07* | (2006.01) |

(52) U.S. Cl. .......................... 514/556; 514/561; 514/725
(58) Field of Classification Search .................. None
    See application file for complete search history.

(56) References Cited

U.S. PATENT DOCUMENTS

| | | |
|---|---|---|
| 4,453,941 A | 6/1984 | Jacobs |
| 5,051,449 A | 9/1991 | Kligman |
| 6,767,924 B2 * | 7/2004 | Yu et al. .................... 514/557 |

FOREIGN PATENT DOCUMENTS

| | | |
|---|---|---|
| WO | WO 93/19743 A1 | 10/1993 |
| WO | WO 02/02074 A2 | 1/2002 |

OTHER PUBLICATIONS

Ding-Dar, et al. (2009) Journal of Cellular Physiology, 220: 427-39.*
Nelson, et al. (2006) Journal of Investigative Dermatology, 126(10) 2178-89.*

* cited by examiner

*Primary Examiner* — Robert M Kelly

(57) ABSTRACT

The present invention relates to a composition including at least one retinoid and at least one beta-aminoisobutyric acid derivative and the use thereof for the preparation of an article to be used for the topical application to skin, hair or nails.

8 Claims, No Drawings

COMPOSITIONS CONTAINING RETINOID AND BETA-AMINOISOBUTYIC ACID DERIVATIVES

BACKGROUND OF THE INVENTION

The human skin is subject to certain aging processes, some of which are attributable to intrinsic processes (e.g., chronoaging) and some of which are attributable to exogenous factors (e.g., photo-aging). In addition, temporary or even lasting changes to the skin can occur, such as acne greasy or dry skin, keratoses, rosacea, light-sensitive, inflammatory, erythematous, and allergic or autoimmune-reactive reactions, such as dermatosis and photodermatosis.

The consequences of the above-mentioned ageing processes can include thinning of the skin, weaker interlacing of epidermis and dermis, and a reduction in the number of cells and the supplying blood vessels. This often results in the formation of fine lines and wrinkles, and pigment defects can occur.

Retinoids, such as retinoic acid, retinol and esters thereof, and tazorotene, act on the differentiation of epithelial cells and are therefore employed for the prophylaxis and treatment of numerous phenomena, which impair the skin state. For example use against acne, psoriasis, senile keratosis, skin discoloration and wrinkles has been described. See, e.g., PCT Patent Applications Nos. WO 93/19743 and WO 02/02074.

Applicants have unexpectedly discovered that beta-aminoisobutyric acid and its derivatives induce a significant, synergistic increase of retinoid activity.

SUMMARY OF THE INVENTION

The present invention relates to a composition including (i) at least one retinoid and (ii) at least one compound of Formula I or a salt or ester thereof, and the use thereof for the preparation of an article to be used for the topical application to skin, hair or nails.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

DEFINITIONS

As used herein, "topical application" and "topically applying" means directly laying on or spreading on the skin, hair, or nail in need of treatment, e.g., by use of the hands or an applicator such as a wipe.

As used herein, "cosmetically-acceptable" means that cosmetically active agents, inert ingredients, or composition which the term describes are suitable for use (e.g., as a cosmetic or pharmaceutical) in contact with tissues (e.g., the skin) without undue toxicity, incompatibility, instability, irritation, allergic response, and the like, commensurate with a reasonable benefit/risk ratio.

Retinoids

The compositions of the present invention contain one or more retinoids. Examples of retinoids include, but are not limited to, retinol, retinoic acid, retinal, and salts and esters thereof, such as retinyl palmitate, retinyl propionate, and retinyl acetate. In one embodiment, the composition contains retinol, such as all-trans-retinol. Other retinoids are disclosed in U.S. Pat. No. 5,051,449. Mixtures of two, three or more retinoids can be used with the compositions of the present invention.

In one embodiment, the composition includes a cosmetically-acceptable amount of the retinoid(s). The retinoid(s) typically will be present in the composition in an amount of at least 0.001%, preferably from about 0.001% to about 5% by weight, and in particular in an amount from about 0.005% to about 2% by weight, such as from about 0.01% to about 0.5%.

Beta-Aminoisobutyric Acid and its Derivatives

The compositions of the present invention contain one or more compounds of Formula I or a salt or ester thereof

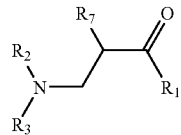

Formula I wherein:

$R_1$ is —O—$R_4$ or

$R_2$, $R_3$, $R_5$ and $R_6$, independently, are selected from the group consisting of H, —OH, alkoxy, a straight-chain or branched $C_1$- to $C_{20}$-alkyl group (wherein the alkyl group is optionally interrupted by oxygen) such as methyl, ethyl, n- or -iso-propyl, n-, iso- or tert-butyl, pentyl, hexyl, heptyl, octyl or nonyl, a straight-chain or branched $C_3$- to $C_{20}$-alkenyl group, such as propenyl or butenyl, and a straight-chain or branched $C_1$- to $C_{20}$-hydroxyalkyl group (wherein the hydroxyl group is optionally bonded to a primary or secondary carbon atom of the alkyl group and wherein the alkyl group is optionally interrupted by oxygen);

$R_4$ is selected from the group consisting of H, a straight-chain or branched $C_1$- to $C_{20}$-alkyl group (wherein the alkyl group is optionally interrupted by oxygen) such as methyl, ethyl, n- or -iso-propyl, n-, iso- or tert-butyl, pentyl, hexyl, heptyl, octyl or nonyl, a straight-chain or branched $C_3$- to $C_{20}$-alkenyl group, such as propenyl or butenyl, and a straight-chain or branched $C_1$- to $C_{20}$-hydroxyalkyl group (wherein the hydroxyl group is optionally bonded to a primary or secondary carbon atom of the alkyl group and wherein the alkyl group is optionally interrupted by oxygen); and R7 is a straight-chain or branched $C_1$- to $C_6$-alkyl group, in particular methyl.

In one embodiment, $R_1$ is —O—$R_4$. In a further embodiment, $R_4$ is H or a straight-chain or branched $C_1$- to $C_6$-alkyl group (wherein the alkyl group is optionally interrupted by oxygen), such as methyl, ethyl, propyl, isopropyl, butyl, and t-butyl.

In one embodiment, $R_2$, $R_3$, $R_5$ and $R_6$, independently are H or a straight-chain or branched $C_1$- to $C_6$-alkyl group (wherein the alkyl group is optionally interrupted by oxygen), such as methyl, ethyl, propyl, isopropyl, butyl, and t-butyl.

In one embodiment, the compound is beta-aminoisobutyric acid ("BAIBA") or a salt or ester thereof, in particular the methyl, ethyl, propyl, isopropyl, butyl, and t-butyl ester.

In one embodiment, the composition includes a cosmetically-acceptable amount of the compound(s) of Formula I or a salt or ester thereof. In one embodiment such compound(s) can be present in the composition in an amount from about 0.001% to about 100 by weight, in particular in an amount from about 0.01% to about 5% by weight, such as from about 0.1% to about 1%.

Carnitine

The compositions of the present invention can further contain one or more compounds selected from carnitine or a salt or ester thereof.

In one embodiment, the composition includes a cosmetically-acceptable amount of the compound(s) selected from carnitine or a salt or ester thereof. In one embodiment such compound(s) can be present in the composition in an amount of at least 0.001%, preferably from about 0.001% to about 10% by weight, and in particular in an amount from about 0.01% to about 5% by weight, such as from about 0.05% to about 1%.

Salts

The compounds of the present invention such as the retinoids, compounds of Formula I, or carnitine may also be present in the form of cosmetically-acceptable salts. For use in medicine, the salts of the compounds of this invention refer to non-toxic "cosmetically-acceptable salts," cosmetically-acceptable acidic/anionic or basic/cationic salts. Cosmetically-acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Cosmetically-acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically-acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Topical Compositions

The composition and products containing such compositions of the present invention may be prepared using methodology that is well known by an artisan of ordinary skill.

The compositions useful in the present invention involve formulations suitable for topically administering to the target tissues, such as mammalian skin such as human skin. In one embodiment, the composition contains a cosmetically-acceptable amount of (i) one or more retinoids, such as retinol, (ii) one or more compounds selected from BAIBA or a salt or ester thereof, (iii) optionally, one or more compounds selected from carnitine or a salt or ester thereof, and (iv) a cosmetically-acceptable carrier, such as an emulsion.

The compositions may be made into a wide variety of articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like. These product types may contain several types of cosmetically-acceptable carriers including, but not limited to solutions, suspensions, emulsions such as microemulsions and nanoemulsions, gels, solids and liposomes. Such articles may be distributed as a pharmaceutical, an over-the-counter medication, or cosmetic. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically-acceptable aqueous or organic solvent). Examples of suitable organic solvents include but are not limited to propylene glycol, polyethylene glycol (e.g. 200-600), polypropylene glycol (e.g. 425-2025), glycerol 1,2,4-butanetriol, sorbitol esters, 1,2,6-hexanetriol, ethanol, and mixtures thereof.

A lotion can be made from such a solution. Lotions typically contain from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, typically from about 1% to about 10% (e.g., from about 2% to about 5%) of the carrier contains an emulsifier(s). Emulsifiers may be nonionic, anionic, cationic, or zwitterionic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s). Single emulsion skin care preparations, such as lotions and creams, of the oil-in-water type and water-in-oil type are well-known in the art and are useful in the subject invention, including but not limited to silicone-in-water and water-in-silicone emulsions. Multiphase emulsion compositions, such as the water-in-oil-in-water type or the oil-inwater-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

The compositions of the present invention can also be formulated into a solid formulation (e.g., a wax-based stick, soap bar composition, powder, and wipe containing powder).

The composition of the present invention can also be formulated as a suspension, including but not limited to, a solid lipid nanonized particle suspension.

The compositions useful in the subject invention may contain, in addition to the aforementioned components, a wide variety of additional oil-soluble materials and/or water-soluble materials conventionally used in compositions for use on skin at their art-established levels.

Additional Active Agents

In one embodiment, the topical composition further includes additional active agent(s). What is meant by an "active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning. Active agents include cosmetic and pharmaceutical active agents.

In one embodiment, the active agent is selected from, but not limited to, the group consisting of hydroxy acids, benzoyl peroxide, sulfur resorcinol, caffeine, ascorbic acid, D-panthenol, hydroquinone, octyl methoxycinnimate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, soy, climbing ivy (Hedera helix), arnica (Arnica Mont.), rosemary (*Rosmarinus officinalis* N), sage (*Salvia officinalis* N), ginseng (*Panax ginseng*), St. Johns-wart (*Hypericum perforatum*), ruscus (*Ruscus aculatus*), meadowsweet (*Filipendula ulmaria* L), and orthosiphon (*Ortosifon stamincus* Benth), Forskolin, and derivatives and mixtures thereof.

In one embodiment, the composition further contains a vitamin in addition to the retinoid. Examples of vitamins include, but are not limited to, vitamin Bs (such as vitamin B3, vitamin B5, and vitamin B12), vitamin C, vitamin K, and vitamin E, and derivatives thereof.

In one embodiment, the composition also contains an antioxidant. Examples of antioxidants include, but are not limited to, water-soluble antioxidants such as sulfhydryl compounds and their derivatives (e.g., sodium metabisulfite and N-acetylcysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopheryl acetate), tocotrienols, and ubiquinone. Natural extracts containing antioxidants suitable for use in the compositions of this invention, include, but are not limited to, extracts containing flavonoids and isoflavonoids and their derivatives (e.g., genistein and diadzein), extracts containing resveratrol and the like. Examples of such natural extracts include grape seed, green tea, pine bark, and propolis.

The active agent will typically be present in the composition of the invention in an amount of from about 0.001% to about 20% by weight of the composition, e.g., about 0.01% to about 10% such as about 0.1% to about 5%.

Other Materials

Various other cosmetically-active agents may also be present in the skin care products. These include, but are not limited to, skin protectants, humectants, and emollients. The composition may also include chelating agents (e.g., EDTA), preservatives (e.g., parabens), pigments, dyes, opacifiers (e.g., titanium dioxide), and fragrances.

The composition and products containing such compositions of the present invention may be prepared using methodology that is well known by an artisan of ordinary skill.

Uses

The composition according to the invention can be used to treat a variety of hair, nail and skin conditions, such as (i) reducing the appearance of the signs of aging (e.g., reducing the appearance of wrinkles and fine lines), cellulite, stretchmarks, light or dark areas, pores, and oil on the skin and (ii) treating dry skin and acne, and (iii) enhancing the firmness and/or elasticity of the skin.

EXAMPLES

The present invention will be further illustrated below by way of Examples, but the present invention is not limited thereto.

Example 1

Topical Gel Compositions

The four topical gel copositions of Table 1 were manufactured as follows.

TABLE 1

| INGREDIENT | "PLACEBO PRODUCT" | RETINOL PRODUCT" | "BAIBA PRODUCT" | "RETINOL AND BAIBA PRODUCT" |
| --- | --- | --- | --- | --- |
| | %, BY WEIGHT OF COMPOSITION | | | |
| Deionized Water | q.s. 100% | q.s. 100% | q.s. 100% | q.s. 100% |
| Disodium EDTA | 0.1% | 0.1% | 0.1% | 0.1% |
| C10-30 Alkyl acrylates crosspolymer | 0.35% | 0.35% | 0.35% | 0.35% |

TABLE 1-continued

| INGREDIENT | "PLACEBO PRODUCT" | "RETINOL PRODUCT" | "BAIBA PRODUCT" | "RETINOL AND BAIBA PRODUCT" |
|---|---|---|---|---|
| | %, BY WEIGHT OF COMPOSITION | | | |
| Sodium hydroxide | 0.12% | 0.12% | 0.12% | 0.12% |
| Methylparaben | 0.25% | 0.25% | 0.25% | 0.25% |
| Propylparaben | 0.1% | 0.1% | 0.1% | 0.1% |
| Octyl palmitate | 5% | 5% | 5% | 5% |
| BHT | 0.07% | 0.07% | 0.07% | 0.07% |
| Phenoxyethanol | 0.5% | 0.5% | 0.5% | 0.5% |
| Retinol 46%/Polysorbate 20 54% | — | 0.09% | — | 0.09% |
| DL-3-Aminoisobutyric acid | — | — | 1% | 1% |

A water phase was made by adding and mixing the C10-30 alkyl acrylates crosspolymer with the water while heating the mixture to 75° C. During the heating process, both the disodium EDTA and sodium hydroxide solutions were added. At 75° C., the methylparaben, propylparaben, and phenoxyethanol were added as a mixture. An oil phase was made by separately heating BHT and octyl palmitate to 75° C. and then mixing them together. The oil phase was then added to the water phase and the resulting mixture was then cooled to about 30° C., upon which any remaining ingredients were added.

Example 2

Enhancement of Retinoid Activity

The four topical gel products of Example 1 where tested for their ability to enhance human cell proliferation. Skin explants were obtained from human abdominal biopsies obtained from plastic surgery procedures. The skin explants were punched and cultivated in a maintenance medium. The four products were applied to the explants once a day. Following two days of treatment, cell proliferation in the explants was measured by detecting the expression of Ki67 protein, a specific marker of cell proliferation, in basal keratinocytes from the treated cells using a specific monoclonal antibody. Cells positive for Ki 67 expression were counted, and the results are expressed as the percent of change in the number of Ki67 positive cells per cm induced by the different treatments versus placebo. The results of the assay are depicted in Table 2.

TABLE 2

| TEST PRODUCT | NUMBER OF MITOTIC CELLS/CR OVER PLACEBO |
|---|---|
| Placebo Product | — |
| Retinol Product | 68.3* |
| BAIBA Product | −1.8 |
| Retinol and BAIBA Product | 278*,# |

*Significant difference vs. placebo (p < 0.05)
Significant difference vs. Retinol product (p < 0.05)

The Retinol Product showed a slight but significant increase in cell proliferation as compared to the placebo product. On the contrary, the BAIBA Product did not increase cell proliferation as compared to the placebo product. Applicants, however, unexpectedly found that the Retinol and BAIBA Product induced a significant, synergistic increase of retinol activity, as evident by the four-fold increase in cell proliferation.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A composition comprising (i) at least one retinoid and (ii) at least one compound of Formula I or a salt or an ester thereof:

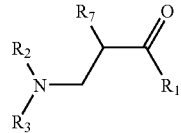

Formula I wherein:
$R_1$ is —O—$R_4$ or

$R_2$, $R_3$, $R_5$ and $R_6$, independently, are selected from the group consisting of H, —OH, alkoxy, a straight-chain or branched $C_1$- to $C_{20}$-alkyl group (wherein the alkyl group is optionally interrupted by oxygen), a straight-chain or branched $C_3$- to $C_{20}$-alkenyl group, and a straight-chain or branched $C_1$- to $C_{20}$-hydroxyalkyl group (wherein the hydroxyl group is optionally bonded to a primary or secondary carbon atom of the alkyl group and wherein the alkyl group is optionally interrupted by oxygen);

$R_4$ is selected from the group consisting of H, a straight-chain or branched $C_1$- to $C_{20}$-alkyl group (wherein the alkyl group is optionally interrupted by oxygen), a straight-chain or branched $C_3$- to $C_{20}$-alkenyl group, and a straight-chain or branched $C_1$- to $C_{20}$-hydroxyalkyl group (wherein the hydroxyl group is optionally bonded to a primary or secondary carbon atom of the alkyl group and wherein the alkyl group is optionally interrupted by oxygen); and R7 is a straight-chain or branched $C_1$ to $C_6$-alkyl group.

2. A composition according to claim 1, wherein said compound of Formula I is beta-aminoisobutyric acid or a salt or an ester thereof.

3. A composition according to claim 2, wherein said composition comprises from about 0.001% to about 2% by weight of said retinoid and from about 0.001% to about 10% by weight of said beta-aminoisobutyric acid or salt or ester thereof.

4. A composition according to claim 1, wherein said compound of Formula I is beta-aminoisobutyric acid.

5. A composition according to claim 1, wherein said retinoid is retinol.

6. A composition according to claim 1, wherein said composition further comprises carnitine or salt or ester thereof.

7. A composition according to claim 6, wherein said composition further comprises from about 0.001% to about 10% by weight of said carnitine or salt or ester thereof.

8. A composition according to claim 1, wherein said composition further comprises a carrier selected from the group consisting of solutions, suspensions, emulsions, gels, solids and liposomes.

\* \* \* \* \*